United States Patent [19]

Suzuki et al.

[11] Patent Number: 4,729,237

[45] Date of Patent: Mar. 8, 1988

[54] TUNING FORK VIBRATION-TYPE VISCOSITY MEASURING APPARATUS

[75] Inventors: Osamu Suzuki, Kumagaya; Syousuke Ishiwata, Saitama; Mitsuroh Hayashi, Kumagaya, all of Japan

[73] Assignee: Chichibu Cement Kabushiki Kaisha, Tokyo, Japan

[21] Appl. No.: 941,060

[22] Filed: Dec. 12, 1986

[30] Foreign Application Priority Data

Dec. 12, 1985 [JP] Japan .................. 60-277939

[51] Int. Cl.$^4$ .............................................. G01N 11/16
[52] U.S. Cl. ........................................................ 73/54
[58] Field of Search ............................................ 73/54

[56] References Cited

U.S. PATENT DOCUMENTS 4,602,505  7/1986  Kanda et al. ........................ 73/54

FOREIGN PATENT DOCUMENTS 135337   8/1982  Japan ........................ 73/54
166840   9/1984  Japan ........................ 73/54
344334  10/1972  U.S.S.R. .................... 73/54
612160   6/1978  U.S.S.R. .................... 73/54
989384   1/1983  U.S.S.R. .................... 73/54

Primary Examiner—Stewart J. Levy
Assistant Examiner—Joseph W. Roskos
Attorney, Agent, or Firm—Bruce L. Adams; Van C. Wilks

[57] ABSTRACT

A vibration-type viscosity measuring apparatus having a pair of vibrator subassemblies that can be resonated as a tuning fork. Each of the pair of vibrator subassemblies constituting a tuning fork has at its free end a sensor plate comprised of a thin metal plate to be inserted into a sample. Each vibrator subassembly has a center line of vibration about which the vibrator subassembly vibrates and a center of gravity aligned on the center line of vibration. A detector is provided for detecting electrically the vibration amplitude of the vibrator subassemblies that are driven together with the sensor plates at the same frequency in reverse phase relation to each other. The vibration amplitude is changed due to the viscosity resistance of the sample applied to the sensor plates. A thermometer probe is provided at the intermediate point between the sensor plates and can be inserted together with the pair of sensor plates into the sample thereby simultaneously measuring the viscosity and the temperature of the sample.

25 Claims, 5 Drawing Figures

FIG. 1
FIG. 2
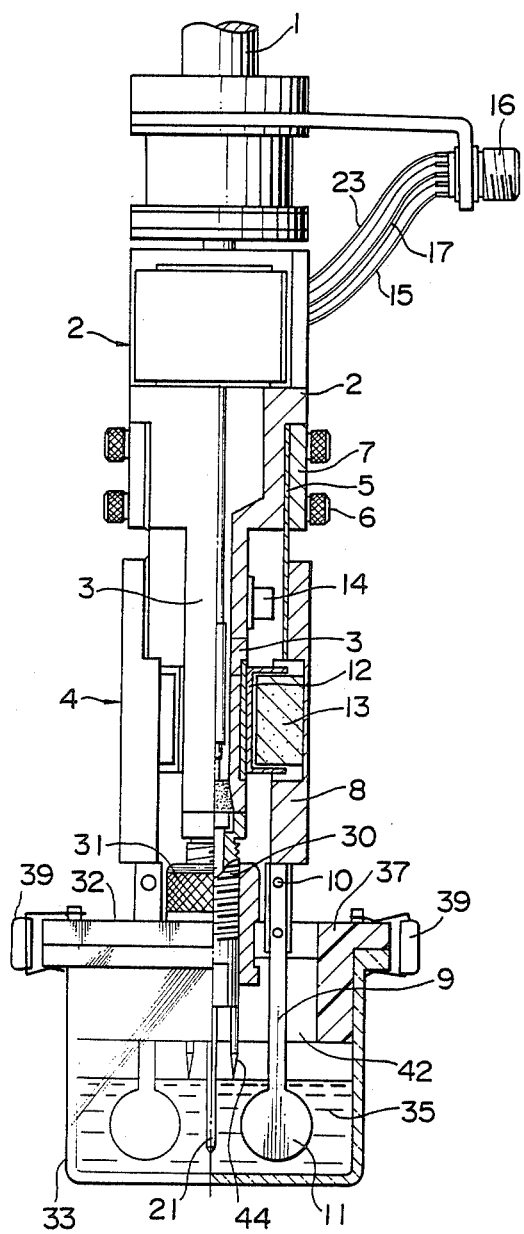
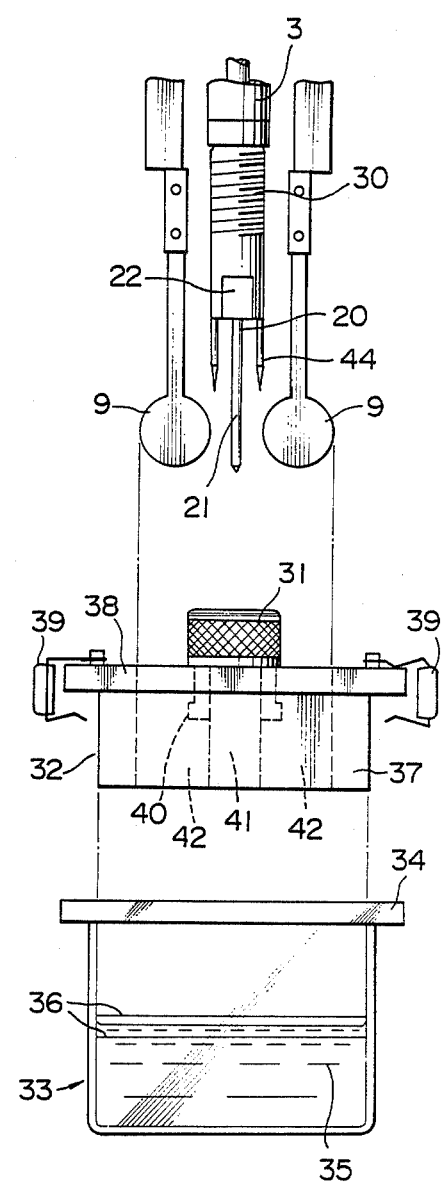

FIG. 3
FIG. 4
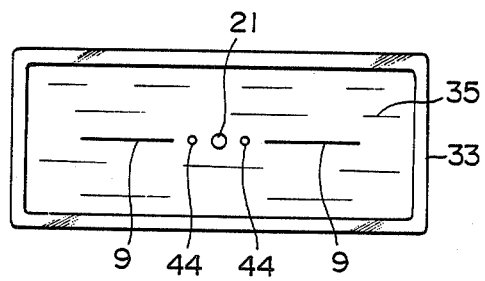
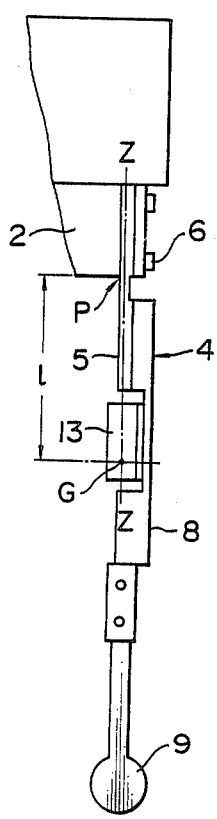
FIG. 5
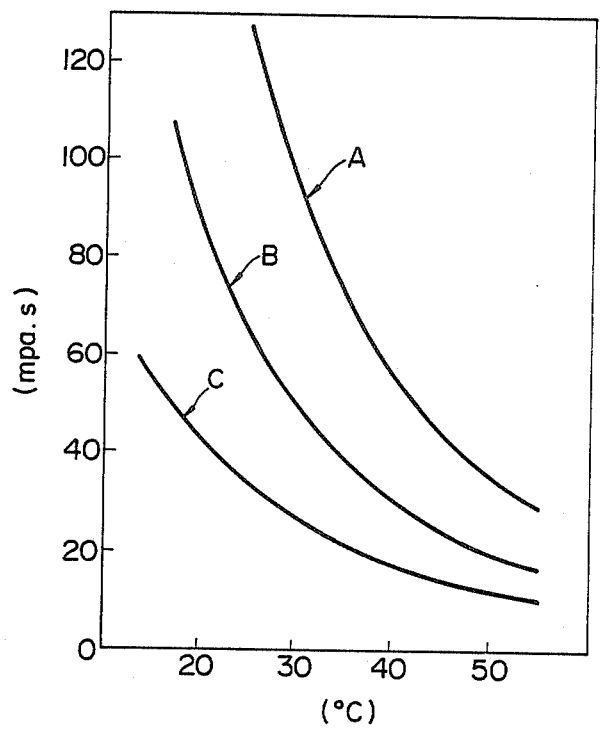

TUNING FORK VIBRATION-TYPE VISCOSITY MEASURING APPARATUS

FIELD OF THE INVENTION

The present invention relates to a vibration-type viscosity measuring apparatus, and more particularly, to a vibration-type viscosity measuring apparatus for measuring the viscosity of a sample equipped with a tuning fork-like member capable of being vibrated in the sample by measuring the amplitude of the member to detect the viscosity resistance of the sample that is applied to the tuning fork-like member.

BACKGROUND OF THE INVENTION

U.S. Pat. No. 4,602,505 (corresponding to European Patent Publication No. 112156A), entitled "APPARATUS FOR MEASURING VISCOSITY", and issued June 29, 1986 to the inventors, proposes a viscosity measuring apparatus that uses a tuning fork vibrating member of a new idea instead of the conventional single vibrating member type viscosity measuring apparatus. In the single vibrating member type viscosity measuring apparatus, the reaction due to the vibrations of the vibrating member is induced in the support for supporting the vibrating member, resulting in the change in the amplitude value of the vibrating member, and as a result, it is impossible to obtain a high accuracy of the measurement. On the other hand, in the tuning fork vibration type viscosity measuring apparatus, since the apparatus has a pair of vibrating members which are driven in inverse phase relation to each other, the pair of the vibrating members can be operated in a resonance state, and therefore the reaction applied to the support due to the vibrations is little or can be reduced to a negligible degree, resulting in substantial improvement in the accuracy of the measurement.

Further study seeking a higher accuracy of measurement has been continued and necessity for improvements of the above tuning fork vibration type viscosity measuring apparatus has become apparent. One of the improvements is to measure the temperature of a sample quickly and accurately so as to make clear the relative relation between viscosity and temperature as in the case of other types of viscosity measuring apparatuses. Another improvement is to keep the depth of vibrating members in a sample liquid constant to solve the problem of the change in the measured value of the viscosity due to the difference of the depth of the vibrating members immersed in a sample liquid. Other remaining improvements include, for example, the design of the structure of the vibrating members and the way of supporting the vibrating members, almost of all of the problems have been solved and the new tuning fork vibration type viscosity measuring apparatuses are being used for the viscosity measurement.

SUMMARY OF THE INVENTION

An object of the present invention is to provide a tuning fork vibration type viscosity measuring apparatus equipped with a thermometer capable of measuring continuously the viscosity as well as the temperature of the sample quickly and accurately to determine the relative relation between the viscosity and the temperature of the sample.

Another object of the present invention is to provide a tuning fork vibration type viscosity measuring apparatus wherein a pair of vibrating members can be immersed in a sample, and at the same time a thermometer can be immersed in sample, and the the immersed depth of the pair of vibration members and the thermometer in the sample can be simultaneously adjusted.

According to the present invention, a vibration-type viscosity measuring apparatus can be provided, wherein a pair of vibrator subassemblies constitute a tuning fork vibrator, each of the vibrator subassemblies has a sensor plate comprising a thin metal plate whose free end will be inserted into a sample to be measured, a detector is provided for detecting electrically the amplitude of the vibrator subassemblies that will vary due to the viscosity resistance of the sample applied to the sensor plates, the vibrator subassemblies as well as the sensor plates are driven at the same frequency in reverse phase relation to each other, and a thermometer probe is provided at an intermediate point between the sensor plates, so that by means of the thermometer probe and the pair of sensor plates inserted into the sample, the viscosity and the temperature of the sample can be simultaneously measured.

According to the present invention, a viscosity measuring apparatus for measuring the viscosity and the temperature of a sample at the same time can be provided, which comprises a support block firmly fixed to a base frame and having a support column at the lower section, tuning fork vibrator means fixed to the support block, extending downward from the support block, and including a pair of vibrator subassemblies arranged on opposite sides of the support column, each of the vibrator subassemblies having at its free end a flat sensor plate that will be inserted into the sample to be measured, means for driving the pair of vibrator subassemblies at the same frequency in reverse phase relation to each other, means for detecting the amplitude of the pair of vibrator subassemblies that will change due to the viscosity resistance applied to by the sensor plates inserted in the sample and for converting the amplitude into an electrical signal, and a thermometer secured to the lower end of the support column, situated at an intermediate point between the sensor plates of the pair of vibrator subassemblies, arranged in an imaginary vertical plane where the sensor plates are arranged, and having a probe that will be inserted together with the sensor plates into the sample, so that the change in the viscosity of the sample due to the change in the temperature of the sample can be measured continuously.

According to a preferred embodiment of the present invention, a carrier apparatus that carries a sample container is mounted at the lower end section of the support column, the sample container is attached detachably to the carrier apparatus, and the carrier apparatus is mounted slidably axially of the support column in such a way that the sample container can be moved vertically with respect to the support column. In this case, the support column has level indicating pins extending downward from the end section of the support column, and the carrier apparatus includes means for adjusting the height of the carrier apparatus in the axial direction of the support column so that the ends of the indicating pins may be in registry with the surface of the sample in the sample container.

BRIEF DESCRIPTION OF THE INVENTION

FIG. 1 is a partial cut-away side elevational view of a viscosity measuring apparatus according to the present invention;

FIG. 2 is an exploded side elevational view of the carrier apparatus shown in FIG. 1;

FIG. 3 is a side elevational view of the vibrator subassembly shown in FIG. 1;

FIG. 4 is a plan view illustrating the relative positional relation of the sensor plates, the thermometer and the level indicating pins in the sample container; and FIG. 5 is a graph illustrating the relation between the viscosity and the temperature of three samples.

DETAILED DESCRIPTION OF THE PREFERRED EMBODIMENT

Referring to FIG. 1, a vibration-type viscosity measuring apparatus according to the present invention is provided with a hollow support block 2 of a rigid material firmly fixed to a frame shaft 1 extending from a base (not shown), and the support block 2 has a support column or shaft 3 extended downward. A pair of vibrator subassemblies or longitudinal vibrating means 4 constituting a tuning fork-like vibrator is fixed to the lower end section of the support block 2 and is extended downward from the support block 2 so that the vibrator subassemblies 4 are positioned on the opposite sides of the support column 3. Each of the vibrator subassemblies 4 includes a leaf spring 5 whose one end is fixed to the support block 2 by screws 6 via a fastener 7, an intermediate plate 8 firmly attached to the other end of the leaf spring 5 and a sensor flate plate 9 fixed to one end of the intermediate plate 8 by screws 10. The leaf spring 5 is advantageously made of an elastic spring steel and the intermediate plate 8 is preferably made of a relatively rigid light material such as aluminium. The sensor plate 9 is a very thin plate having a thickness in the order of 0.2 mm that may be made of a chemical-resistant stainless steel, and the free end of the sensor plate is in the shape of a disk 11 having a diameter in the order, for example, of 20 mm.

The vibrator subassemblies 4 are arranged symmetrically relative to each other and each of the vibrator subassemblies 4 has above the intermediate plate 8 an electromagnetic coil 12 attached to the support column 3 and a permanent magnet 13 cooperative with the electromagnetic coil 12. Each combination of the electromagnetic coil 12 and the permanent magnet 13 serves as a driving apparatus for vibrating the corresponding vibrator subassembly 4, so that the vibrator subassemblies 4 can be vibrated at the same frequency in reverse phase relation to each other, that is, the phase difference of 180 degrees. According to a preferred embodiment, the driving frequency is 30 Hz, and the of a single vibrator subassembly amplitude is 20 microns under no load at the point where a displacement sensor 14 that will be described hereinafter is attached. The sensor plates 9 arranged in a pair are situated in the same imaginary vertical plane parallel to the support column 3, and as a result, the torsional reaction of the support block 2 that would be induced when they are situated in different vertical planes can be obviated. Although the relative positional arrangement of the electromagnetic coil 12 and the permanent magnet 13 can be reversed, when the electromagnet coil 12 is situated on the side of the support column 3 as in the illustrated embodiment, it is preferable in that a lead wire 12 of the coil 12 can be led through the support column 3 to a terminal fitment 16 (situated upward). If the viscosity measuring apparatus is a small-sized one for measuring a sample having a low viscosity, instead of the electromagnetic driving apparatus, a piezo-electric driving apparatus can be employed.

The displacement detector 14 is provided on the support column 3 between the support block 2 and the electromagnetic coil 12 and is opposed to the leaf spring 5 of the vibrator subassembly 4. The displacement detector 14 operates for converting the vibration amplitude of one of the vibrator assemblies 4 to an electrical signal. In this case, although an additional displacement detector may be provided for the other vibrator subassembly, since both the vibrator subassemblies 4 exhibit substantially the same amplitude, only one displacement detector is sufficient to detect the vibration amplitude. As described hereinafter, when the pair of the sensor plates 9 is inserted into a liquid sample, the amplitude of the vibrator subassemblies 4 is influenced by the change in the viscosity resistance thereof, then this amplitude is detected electrically by the displacement detector 14, and the viscosity of the sample can be calculated from the detected value in known manner. The displacement detector 14 may be, for example, of a known non-contacting eddy currrent loss type, and if this known displacement detector is used, the leaf spring 5 opposed thereto is made of a magnetic spring steel. Instead of the eddy current loss type displacement sensor, a known optical displacement sensor can also be used. A lead wire 17 of the displacement detector 14 is also led to the common terminal fitment 16 through the support column 3.

Referring to FIG. 3, a desirable design of the vibrator subassembly 4 is illustrated. In this embodiment, the center of gravity G of the vibrator subassembly 4 is positioned on the vibration center line Z—Z of the leaf spring 5 about which the vibrator subassembly vibrates, and in this manner the vertical component of force that would result from the reaction of the vibrations of the vibrator subassembly 4 can be prevented from occurring or can be minimized to a substantially negligible extent. Further in this embodiment, the leaf spring 5 is attached at a right angle to the support block 2, and when the leaf spring 5 is attached, the attaching surface of the support block 2 is to fix the leaf spring 5 made smooth and high tensile bolts are used. This arrangement is effective in that the distance L between the vibration fulcrum point P and the center of gravity G is kept constant and in that the error of amplitude due to the substantial change in the vibration distance L that will result from the loosening of the bolts during the course of the vibration can be prevented from occurring.

Turning to FIG. 2, a thermometer indicated generally by reference numeral 20 is attached to the lower end of the support column 3 and a sheathed prove 21 of the thermometer 20 is extended downward. The temperature probe 21 is situated at the intermediate position between the sensor plates 9 arranged in a pair and is also situated in the same imaginary vertical plane as that where the sensor plates 9 are situated, and the lower end of the temperature probe 21 is situated generally in the same imaginary vertical plane as that where the sensor plates 9 are situated. Since the temperature probe 21 is arranged in the same imaginary vertical plane as that where the pair of the sensor plate 9 is situated, a turbulent flow of the sample due to the presence of the temperature probe 21 between the sensor plates can be prevented from occurring. The thermometer 20 may be a known thermometer having a platinum resistance temperature detector in a sheath, and this known thermometer has a circuit unit 22 including an amplifier at the base end of the sheath. A lead wire 23 of the circuit unit 22 is led to the common terminal fitment 16 through the support column 3.

The lower end section of the support column 3 is formed with a male thread 30, and a carrier apparatus 32 having an adjusting nut member 31 threadably engageable with the male thread 30 is attached to the support column 3. The carrier apparatus 32 carries a sample container 33 detachably and serves as a lid for closing the opening of the sample container 33. The sample container 33 is advantageously made of a transparent glass in the form of a beaker, has a flange 34 around the periphery of the opening, and is formed with indications 36 comprising two parallel lines for indicating the allowable volume of the sample 35 to be introduced into the container 33. The carrier apparatus 32 includes a lid member 37, for example, of a synthetic resin excellent in heat insulating property that has dimensions snuggly fittable into the sample container 33, and the lid member 37 has flanges 38. The lid member 37 is provided with a pair of known clamp fitments 39, and when the clamp fitments 39 are engaged with the flange 34 of the sample container 33, the sample container 33 can be attached to the carrier apparatus 32. Although the adjusting nut member 31 threadably engaged with the male thread 30 is supported rotatably relative to the lid member 37, the nut member 31 has a stopper 40 at its lower end, so that the axial movement of the nut member 31 is restricted by the stopper 40. The lid member 37 is formed with a pair of thin slits 42 for preventing heat from diffusing through which the pair of sensor plates 9 can be passed.

Generally, the carrier apparatus 32 is mounted to the lower end section of the support column 3, and the sample container 33 is attached detachably to the carrier apparatus 32. Two pins 44 are fixed to the lower end of the support column 3 to extend downward, are positioned as shown in FIG. 4 on the opposite sides of the temperature probe 21 and between the probe 21 and the sensor plates 9, and are arranged in the imaginary vertical plane where the sensor plates 9 and the temperature probe 21 are arranged. The tips of the pins 44 have a role as an indicator for indicating a desired surface level of the sample 35 in the container 33 so that the height of the sample container 33 relative to the support column 3 can be determined. Namely, according to the registration between the tips of the pins 44 and the surface level of the sample 35, the adjusting nut member 31 of the carrier apparatus 32 is rotated to move the sample container 33 together with the carrier apparatus 32 axially with respect to the support column 3 to adjust the depth of the sensor plates 9 within the sample 35. As a result, such a troublesome operation for introducing a precisely determined amount of a sample into the sample container 33 would not be required, and even if different amounts of a sample within the allowable range between the two indication lines 36 marked on the sample container 33 are introduced, the sensor plates 9 and the temperature probe 21 can be inserted at definite depths into the sample at all times so that an error of measurement due to the difference between the inserted depths of them can be prevented.

FIG. 5 is a graph showing the results of measurements of known three calibration standard solutions A, B and C by using a viscosity measuring apparatus produced in accordance with the present invention, in which the measured viscosities (in mPa.S) are plotted as ordinate and the temperatures (in °C.) are plotted as abscissa. The above standard solutions A, B and C are types JS200, JS100 and JS50 defined in Japanese Industrial Standards, and after these standard solutions are heated to 60° C., they are measured while they are allowed to cool spontaneously. Thus, by the viscosity measuring apparatus of the present invention, it is possible to measure continuously the change in the viscosity resulting from the change in the temperature. According to the preferred embodiment described herein, a viscosity measuring apparatus can be used for measuring liquids having a viscosity in the range of from 1 mPa.S to 100 Pa.S.

What is claimed is:

1. A vibration-type viscosity measuring apparatus having a measuring unit for measuring the viscosity and the temperature of a sample at the same time, said measuring unit comprising:
   (a) a support block firmly fixed to a base frame and having a support column at a lower section of the support block;
   (b) tuning fork vibrator means fixed to said support block and extending downward from the support block, said tuning fork vibrator means including a pair of vibrator subassemblies arranged on opposite sides of said support column, each of the vibrator subassemblies having a center line of vibration about which the vibrator subassembly vibrates and a center of gravity arranged on the center line of vibration, each vibrator subassembly including at its free end a thin flat sensor plate placeable in a sample during the measurement of the sample viscosity, each sensor plate being arranged in the same imaginary vertical plane;
   (c) means for driving said pair of vibrator subassemblies at the same frequency in reverse phase relation to each other;
   (d) means for detecting the vibration amplitude of said pair of vibrator subassemblies which changes due to a viscosity resistance applied to the sensor plates when placed in the sample and for converting the vibration amplitude into an electrical signal; and
   (e) a thermometer secured to the lower end of said support column, situated at an intermediate point between said sensor plates of said pair of vibrator subassemblies, and arranged in the same imaginary vertical plane where the sensor plates are arranged, the thermometer having a probe which can be immersed together with the sensor plates into the sample.

2. A vibration-type viscosity measuring apparatus as claimed in claim 1, further including:
   (f) a sample container for containing the sample to be measured; and
   (g) adjusting means for adjusting a relative distance between the sensor plates and probe and said sample container so that the immersed depths of said sensor plates and the temperature probe in the sample stored in said sample container can be adjusted.

3. A vibration-type viscosity measuring apparatus as claimed in claim 2, wherein said adjusting means includes carrier means mounted movably axially of said support column at the lower end of said support column, the carrier means carrying said sample container detachably so that said sample container can be moved together with said carrier means axially of said support column.

4. A vibration-type viscosity measuring apparatus as claimed in claim 3, wherein said carrier means is provided with a lid member of said sample container, an adjusting nut member supported rotatably on said lid member, having an axial stopper, and being threadably engaged with a male thread formed on the lower end section of said support column so that said adjusting nut member can be moved axially of said support column, and clamp means provided on said lid member for clamping said sample container.

5. A vibration-type viscosity measuring apparatus as claimed in claim 2, further including;
   (h) indicating means for indicating a position of the surface level of said sample stored in said sample container to determine a desirable relative distance between the sensor plates and probe and said sample container.

6. A vibration-type vibration viscosity measuring apparatus as claimed in claim 5, wherein said indicating means comprises two pins extended downward from the lower end of said support column, said pins being situated between said sensor plates and said probe in the same imaginary vertical plane where said sensor plates and said probe are situated.

7. A vibration-type viscosity measuring apparatus as claimed in claim 1, wherein said vibrator subassemblies are fixed to a smooth surface of said support block by high tensile bolts.

8. A vibration-type viscosity measuring apparatus having a measuring unit for measuring the viscosity and the temperature of a sample at the same time, said measuring unit comprising:
   (a) a support block firmly fixed to a base frame and having a support column at a lower section of the support block;
   (b) tuning fork vibrator means fixed to said support block and extending downward from the support block, the tuning fork vibrator means having a pair of vibrator subassemblies arranged on opposite sides of said support column to undergo vibrating movement, each of the vibrator subassemblies having at its free end a thin flat sensor plate placeable in a sample during the measurement of the sample viscosity, each sensor plate being arranged in the same imaginary vertical plane;
   (c) means for driving said pair of vibrator subassemblies at the same frequency in reverse phase relation to each other;
   (d) means for detecting the vibration amplitude of said pair of vibrator subassemblies which varies due to a viscosity resistance applied to the sensor plates when placed in the sample and for converting the vibration amplitude into an electrical signal;
   (e) a thermometer secured to the lower end of said support column, situated at an intermediate point between said sensor plates of the pair of vibrator subassemblies, and arranged in the same imaginary vertical plane where the sensor plates are arranged, the thermometer having a probe which can be immersed in the sample together with the sensor plates;
   (f) a sample container for containing therein the sample to be measured; and
   (g) adjusting means for adjusting a relative distance between said sensor plates and probe and said sample container so that depths of the sensor plates and probe immersed in the sample stored in said sample container can be adjusted, said adjusting means including carrier means mounted movably in an axial direction of said support column at the lower end of said support column, the carrier means detachably carrying thereon said sample container so that said sample container can be moved together with said carrier means in the axial direction of said support column.

9. A vibration-type viscosity measuring apparatus as claimed in claim 8, wherein said carrier means includes a lid member for covering said sample container, an adjusting nut member supported rotatably on said lid member and threadably engaged with a male thread formed on the lower end section of said support column so that said adjusting nut member can be moved axially of said support column, and clamp means provided on said lid member for detachably clamping said sample container.

10. A vibration-type viscosity measuring apparatus as claimed in claim 9, wherein each of the vibrator subassemblies has a center line of vibration about which the vibrator subassembly vibrates and a center of gravity arranged on the center line of vibration.

11. A vibration-type viscosity measuring apparatus as claimed in claim 9, including:
   (h) indicating means for indicating a position of a surface level of said sample stored in said sample container to determine a desirable relative distance between said sensor plates and probe and said sample container.

12. A vibration-type viscosity measuring apparatus as claimed in claim 11, wherein said indicating means comprises two pins extended downward from the lower end of said support column, said two pins being situated between said sensor plates and said probe in the same imaginary vertical plane where said sensor plates and said probe are situated.

13. A vibration-type viscosity measuring apparatus as claimed in claim 9; wherein said vibration subassemblies are fixed to a smooth surface of said support block by high tensile bolts.

14. A vibration-type viscosity measuring apparatus as claimed in claim 8, wherein each of the vibrator subassemblies has a center line of vibration about which the vibrator subassembly vibrates and a center of gravity arranged on the center line of vibration.

15. A vibration-type viscosity measuring apparatus as claimed in claim 8, including
   (h) indicating means for indicating a position of a surface level of said sample stored in said sample container to determine a desirable relative distance between said sensor plates and probe and said sample container.

16. A vibration-type viscosity measuring apparatus as claimed in claim 15, wherein said indicating means comprises two pins extended downward from the lower end of said support column, said two pins being situated between said sensor plates and said probe in the same imaginary vertical plane where said sensor plates and said probe are situated.

17. A vibration-type viscosity measuring apparatus as claimed in claim 8, wherein said vibrator subassemblies are fixed to a smooth surface of said support block by high tensile bolts.

18. An apparatus for measuring a viscosity of a liquid sample, comprising: a support having a shaft extending downwardly from the support; a pair of longitudinal vibrating means fixed to and extending downwardly from the support in opposed relation relative to the shaft to undergo vibrating movement, each of the longitudinal vibrating means having a center line of vibration about which the vibrating means vibrates and a center of gravity aligned on the center line of vibration, the longitudinal vibrating means having at their free ends a respective flat plate lying in and vibrating along the same plane parallel to the shaft; driving means disposed between the pair of vibrating means and the shaft to effect the vibration of the pair of vibrating means at the same frequency in opposite phase relation to each other; detecting means operative when the flat plates are immersed in a liquid sample for detecting a vibration amplitude of the vibrating means indicative of a viscosity of the liquid sample; and sensing means mounted at a lower end of the shaft and disposed in the same plane at an intermediate point between the flat plates for sensing a temperature of the liquid sample in contact with the liquid sample during the measurement of the liquid sample viscosity.

19. An apparatus according to claim 18; wherein the pair of vibrating means comprise a tuning fork vibrator.

20. An apparatus according to claim 18; wherein the support has a smooth surface for mounting thereon respective one ends of the vibrating means and high tensile bolts for fixing the respective one ends of the vibrating means to the smooth surface.

21. An apparatus according to claim 18; including a container for storing therein a liquid sample, and adjusting means for adjusting a relative distance between the flat plates and the container to determine a depth of the flat plates within the liquid sample.

22. An apparatus according to claim 21; wherein the adjusting means includes carrying means mounted movably in the axial direction of the shaft at the lower end of the shaft for detachably carrying the container.

23. An apparatus according to claim 22; wherein the carrying means includes a nut member threadably engaged with a male thread formed at the lower end of the shaft, a lid member connected to the nut member for covering the container and clamping means disposed on the lid member for detachably clamping the container.

24. An apparatus according to claim 21; wherein the adjusting means includes indicating means for indicating a level of the liquid sample stored in the container to determine a desired depth of the flat plates within the liquid sample.

25. An apparatus according to claim 24; wherein the indicating means comprises a pair of pins extending downwardly from the lower end of the shaft and disposed in the same plane between the sensing means and the flat plates.

* * * * *